United States Patent [19]
Frigg et al.

[11] Patent Number: 5,445,641
[45] Date of Patent: Aug. 29, 1995

[54] STORAGE AND DISPENSING DEVICE FOR OSTEOSYNTHETIC FIXATION ELEMENTS

[75] Inventors: Robert Frigg, Davos-Dorf; Rudolf Ambuhl, Filisur, both of Switzerland

[73] Assignee: Synthes, Paoli, Pa.

[21] Appl. No.: 181,166

[22] Filed: Jan. 13, 1994

Related U.S. Application Data

[63] Continuation of Ser. No. 873,810, Apr. 27, 1992, abandoned.

[30] Foreign Application Priority Data

May 10, 1991 [CH] Switzerland ............... 01405/91

[51] Int. Cl.⁶ ............................................... A61B 17/00
[52] U.S. Cl. ........................... 606/86; 606/104; 606/96; 221/113; 221/72
[58] Field of Search ............... 221/82, 264, 113, 119, 221/72, 95; 606/96, 104, 87, 86; 604/62; 310/265, 266; 292/276

[56] References Cited

U.S. PATENT DOCUMENTS

| | | |
|---|---|---|
| 844,431 | 2/1907 | Wehagen .................. 221/82 |
| 2,835,377 | 5/1958 | May et al. . |
| 3,002,514 | 10/1961 | Deyerle .................... 606/96 |
| 3,029,978 | 4/1962 | Gummere ................. 221/113 |
| 3,171,408 | 3/1965 | Childs et al. . |
| 3,242,931 | 3/1966 | Wandrey ................... 221/113 |
| 3,315,669 | 4/1967 | Rhodes ..................... 606/104 |
| 4,119,092 | 10/1978 | Gil ............................. 606/96 |
| 4,150,766 | 4/1979 | Westendorf .............. 221/119 |
| 4,440,168 | 3/1984 | Warren ..................... 606/87 |
| 4,441,492 | 4/1984 | Rydell et al. . |
| 4,444,180 | 4/1984 | Schneider et al. . |
| 4,673,387 | 6/1987 | Phillips ..................... 604/62 |

FOREIGN PATENT DOCUMENTS 0059044 2/1982 European Pat. Off. .

*Primary Examiner*—Robert A. Hafer
*Assistant Examiner*—David J. Kenealy
*Attorney, Agent, or Firm*—Davis Hoxie Faithfull & Hapgood

[57] ABSTRACT

The device for dispensing of bone screws (1) comprises a drum device (3) that can be rotated around its axis (2), with several holes (4) serving as storage chambers for bone screws (1) or other osteosynthesis fixation elements, arranged peripherally and parallel to the axis (2).

9 Claims, 4 Drawing Sheets

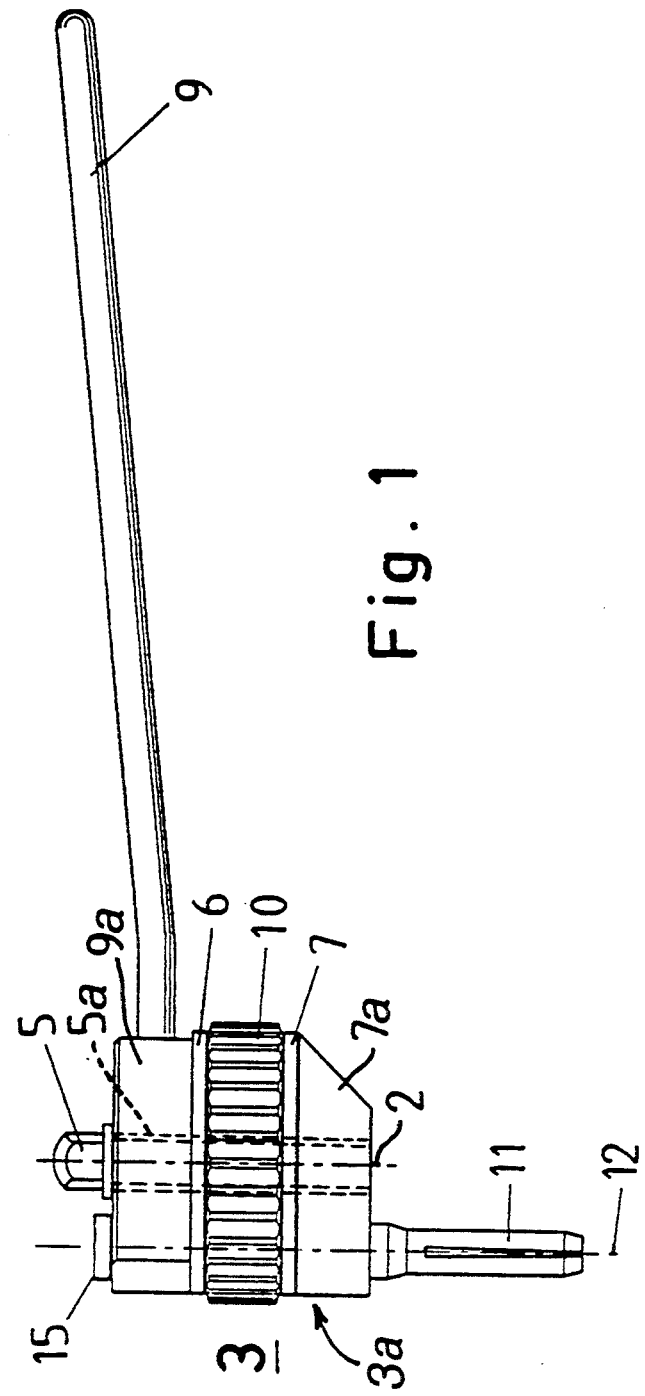

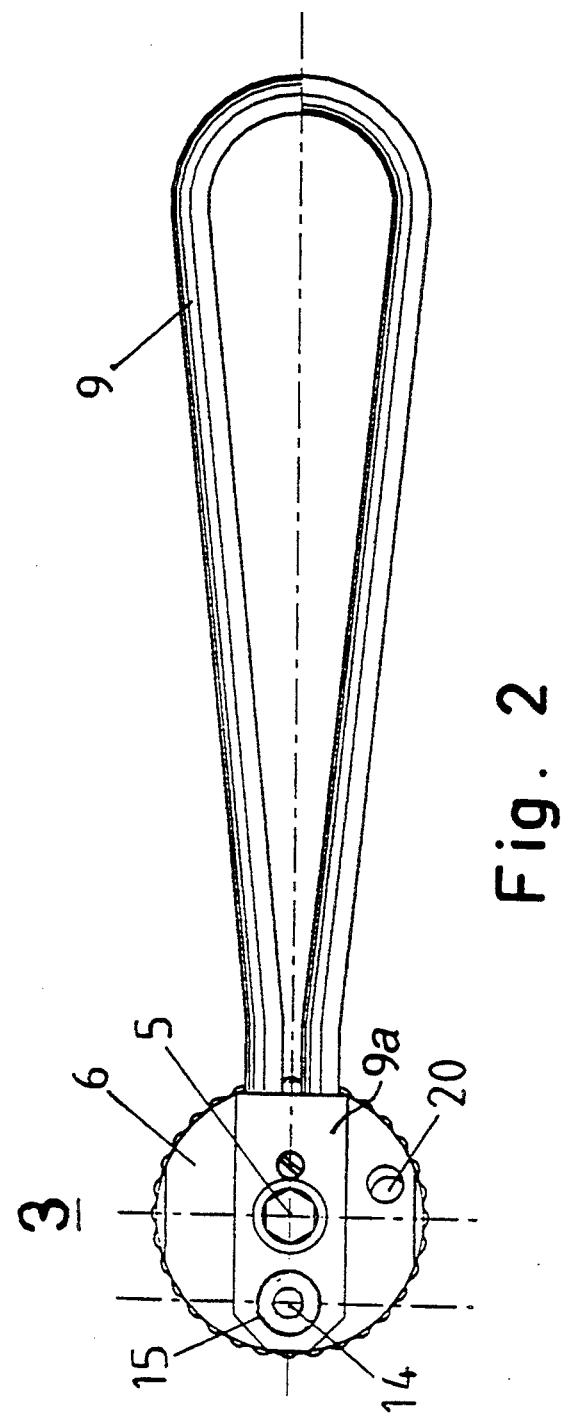

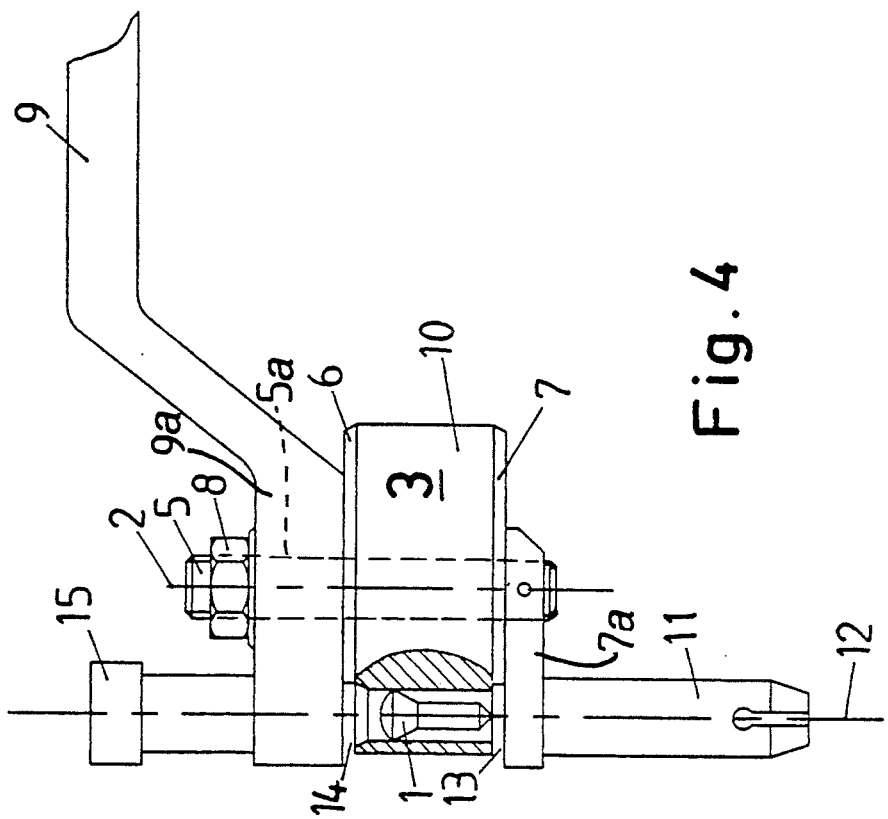
Fig. 4
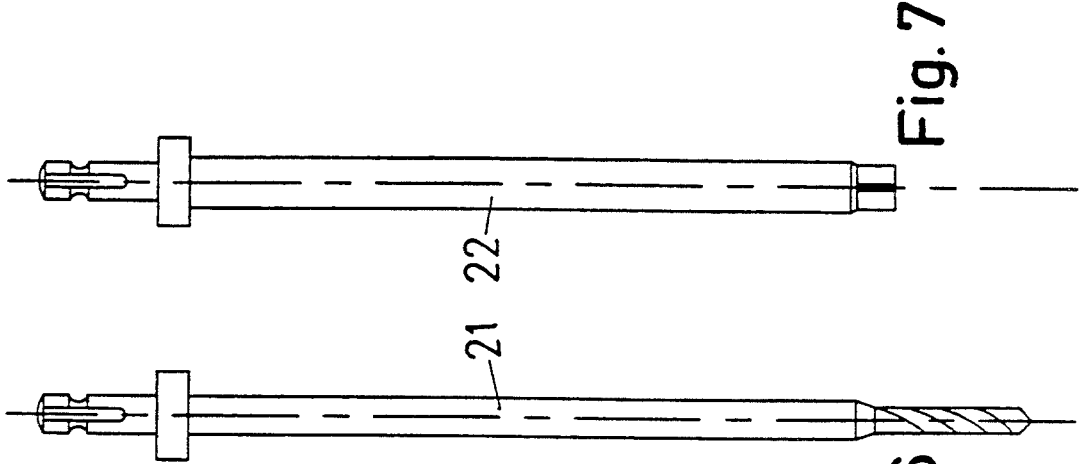
Fig. 6
Fig. 7

1

STORAGE AND DISPENSING DEVICE FOR OSTEOSYNTHETIC FIXATION ELEMENTS

This is a continuation of application Ser. No. 07/873,810 filed on Apr. 27, 1992, abandoned.

FIELD OF THE INVENTION

This invention relates to a device for the storage and dispensing of osteosynthetic fixation elements such as screws.

BACKGROUND OF THE INVENTION

In the surgical treatment of fractures in the maxillofacial area, as well as fractures of the foot and hand, a trend toward preferring ever-smaller implants can clearly be noted. The reason for this is the generally increased understanding of the biomechanical bases of osteosynthesis. In the field of treating maxillofacial fractures, more attention can be paid to the cosmetic results of osteosynthesis, thanks to the miniaturization of implants.

In the field of hand surgery, restrictions on movement in the area of the fingers can be avoided. Osteosynthetic implants in the fingers can be placed under the tendons. In the case of an implant with a large cross-section, the tendons need no longer be extended to their full length.

The dimensions of the so-called mini-implants (screws and plates) are in the area of 0.8 mm–2.0 mm. Problems in the area of packaging, storage and manipulation during surgery arise due to this miniaturization. Handling in the operating room, particularly in the maxillofacial area, has proved difficult. Depending on the degree of severity of the fracture or correction, up to 40 bone screws may be required. These screws must be taken individually by the operating room nurse from a so-called screw rack, checked for length, placed on a screwdriver and given to the surgeon. The surgeon must, in turn, insert them through the osteosynthesis plate into pre-drilled screw holes. During the transfer of the screw and the attempted insertion of the screw, it often falls off the screwdriver, into the wound or onto the OR floor. The attempt to find a lost screw is often excessively time-consuming, given their dimensions (0.8 mm diameter × 4.0 mm) and extends the time spent in surgery. The frequent loss of screws in the OR, and during packing and sterilization, causes unnecessary costs for the hospital.

An additional problem in dealing with mini-screws arises during their implantation. After the surgeon has selected the osteosynthesis plate proper for the fracture in question, he positions the plate over the fracture. He then drills the hole for the screw (0.5–1.5 mm diameter) through one of the plate holes. After drilling, he takes the screw needed from the OR nurse and screws it into the bone through the plate. The problem here often is finding the core drill hole in the bone, since the bone surface is covered with blood or soft tissue and the plate can slip on the smooth bone surface.

SUMMARY OF THE INVENTION

The present invention overcomes or reduces these problems by means of a device for the constant presentation, dispensation and application of osteosynthetic fixation elements such as bone screws. The invention also includes a package for such elements which enables them to be stored in the operating room and dispensed as needed.

Specifically, the invention provides a device for the storage, dispensing and presentation of osteosynthetic elements comprising a drum device rotatable about a central axis and having a plurality of holes distributed around its periphery, having axes parallel to the central axis and forming chambers for the storage of said elements. The invention also provides a package for such elements comprising a cylindrical drum having chambers around its periphery for the storage of orthopedic inserts, said chambers being essentially parallel to the axis of the drum.

The advantages attained through the invention are that, thanks to the invention, an efficient tool is provided for surgeons, greatly facilitating stock maintenance for osteosynthesis fixation elements, particularly bone screws, their. presentation during surgery and the application of such fixation elements. The device pursuant to the invention also serves, in addition to dispensing the fixation elements, as a hole gauge and guide for the tools such as drill bits or screwdrivers with which the fixation elements, particularly bone screws, are inserted.

One embodiment of the invention, which simultaneously explains the operating principles, is shown in the drawing and will be described below in greater detail.

BRIEF DESCRIPTION OF THE DRAWINGS

FIG. 1 is a view in side elevation of a device pursuant to the invention;

FIG. 2 is a top plan view of a device pursuant to the invention;

FIG. 4 is a view in side elevation and further in vertical section of a device pursuant to the invention, of somewhat different design;

FIG. 6 is a view in elevation of a bone drill for use with a device pursuant to the invention; and FIG. 7 is a view in side elevation of a screwdriver for use with the device pursuant to the invention.

DETAILED DESCRIPTION OF THE INVENTION

Figure 5:
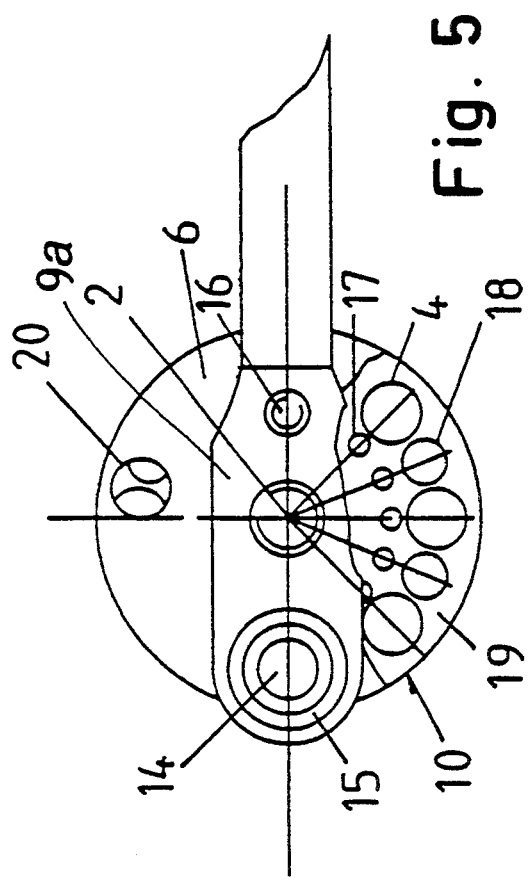
FIG. 5 is a top plan view of a device pursuant to the invention similar to that shown in FIG. 4 with the handle and upper plate partly cut away.
Figure 3:
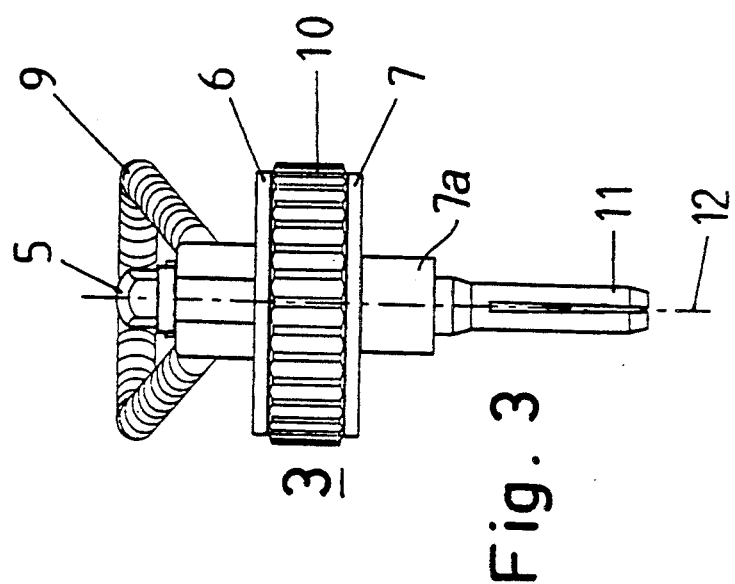
FIG. 3 is a view in front elevation of a device pursuant to the invention.

Referring to FIG. 1, the device 3 comprises a drum housing 3a which includes a lower plate 7, lower plate extension 7a, upper plate 6 and handle extension 9a. Between plates 6 and 7 is positioned a drum 10. A shaft 5a having a boss or hub 5 passes through central apertures in handle extension 9a of upper plate 6 and drum 10. The shaft is fixed in lower plate 7, which in turn is fixed to plate extension 7a. Handle extension 9a and upper plate 6 are not rotatable about shaft 5, as by having a section of the upper end of shaft 5a hexagonal in cross section to match similarly configured apertures in plate 7 and extension 9a. Drum 10, however, is rotatable about the shaft 5a.

On its periphery drum 10 has several series of drilled holes. Holes 4 are designed as chambers to accommodate bone screws 1 (FIG. 4) or other implants. They are parallel to the axis 2 of the shaft 5a.

In addition to the holes 4, a second series of holes 18 are arranged around the periphery. These are located between the holes 4. They are also parallel to the axis of shaft 5a and are at the same radial distance from the axis 2a as the holes 4. They are intended to act as a guide for instruments like drills 21 and screw devices 22 shown in FIGS. 6 and 7.

Finally, the drum has a third series of relatively shallow indentations 17 which are designed to receive a spring-loaded indexing pin or ball.

Upper plate 6, connected solidly to handle 9 through handle extension 9a is provided with access opening 14 for the introduction of instruments 21 and 22, shown in FIGS. 6 and 7. The center of access opening 14 is the same distance from axis 2 as the centers of holes 4 that serve as storage chambers for bone screws 1 and holes 18.

Lower plate 7, connected solidly to shaft 5a, is provided with an outlet opening 13, whose center is the same distance from axis 2 as the center of drill holes 4.

Plate extension 7a of drum housing 3a also has a tissue-protection sleeve 11, through which the core hole can be drilled and bone screw 1 set. The distance of axis 12 of tissue-protection sleeve 11 from axis 2 corresponds to the distance of storage and guide holes 4, 18 in rotary drum 10 from the axis 2.

Upper plate 6, in addition to handle 9, may also be equipped with a drill bushing 15 whose axis corresponds to that of holes 4 and 18 and axis 12 of tissue-protection sleeve 11. In addition, the upper plate has a spring-loaded pin or ball 16 that can seat in indexing indentations 17 of rotary drum 10. Holes 4 and 18 of rotary drum 10 can thus be simply brought into operable relation with tissue-protection sleeve 11 and drill bushing 15.

To assemble the device pursuant to the invention, shaft 5a, connected solidly to lower plate 7, is conducted through the hollow hub of rotary drum 10 and an opening (not shown in the figures) in upper plate 6 and fixed with nut 8 at a distance guaranteeing the rotatability of rotary drum 10 placed between the two plates 6, 7.

The package for bone screws 1 or other fixation elements is thus actually the rotary drum 10 itself. As noted above, the storage holes 4 serve to accept bone screws 1 and smaller guide holes 18 are guides for drills such as 21 for drilling into the bone, as well as guides for screwdrivers 22 for fastening the bone screws 1 in the bone. The indexing sockets 17, applied circularly to the upper side of drum 19, permit the precisely-defined positioning of desired hole 4 or 18 within drum housing 3a.

Rotary drum 10 is easy to change and simultaneously serves as packaging for bone screws 1. As needed, the rotary drum can be offered in a sterile package or it can first be sterilized in the hospital. Instead of replacing rotary drum 10 after it has been emptied, with a new, full rotary drum 10, it can be refilled with bone screws 1 through an additional filling hole 20 in upper plate 6. The center of filling hole 20 must, as a requirement of the design, be at the same distance from axis 2 as the centers of drill holes 4. However, it is offset circumferentially from the holes 4, 18, so that when a drum hole is located below hole 14 in upper plate 6, hole 20 is between holes 4 and 18.

In the following, the manipulation of the device pursuant to the invention during surgery is described:

Rotary drum 10 filled with bone screws 1 is inserted into drum housing 3a without having to handle individual bone screws 1. The surgeon now uses the device pursuant to the invention first as a drill bushing, to drill in the bone the hole into which bone screw 1 is to be inserted. Drill 21 is guided precisely by drill bushing 15 of upper plate 6, through one of smaller guide holes 18 of rotary drum 10 and tissue-protection sleeve 11. The length of the individual guide elements 15, 11 are in agreement with the length of the bore hole. The bore depth into the bone can thus be adapted to the screw length. The tip of tissue-protection sleeve 11 is adapted to the screw holes in the bone plate, whereby the bone plate is pressed onto the bone and thus can no longer slip.

Having made the core drill hole in the bone and after removing drill 21, the surgeon rotates rotary drum 10, by its peripheral knurling, one index position 17. One of the bone screws 1 in rotary drum 10 then moves into the working channel formed by elements 13 and 11. Depending on the construction of storage hole 4 in which bone screw 1 is located, the bone screw may fall through tissue-protection sleeve 11 onto the surface of the bone, or it may be pushed through tissue-protection sleeve 11 onto the bone surface using screwdriver 22. The diameter of screwdriver 22 is adapted to the diameter and design (Phillips, Inbus, etc.) of the head of bone screw 1, so that it is guided over its entire length and forcibly engages the drive of bone screw 1. Since the device pursuant to the invention need not be removed during the entire process, bone screw 1 can be screwed into the bone without searching for the pilot drill hole.

After bone screw 1 is fully inserted, screwdriver 22 is removed and rotary drum 10 is rotated by another index position 17. Thus, a small guide hole 18 of rotary drum 10 is again in work channel 13, 11, so that the next core drill hole can be made. The entire process is repeated until all the screw holes in the plate have been filled with bone screws.

What is claimed is:

1. Apparatus for the storage and presentation of bone screws and like osteosynthesis elements comprising a housing having an upper plate and a lower plate, a shaft, a drum having a peripheral wall rotatably mounted on said shaft in said housing between said upper and lower plates, a plurality of substantially cylindrical storage holes peripherally arranged in said drum inside said peripheral wall, a plurality of substantially cylindrical guide holes having a diameter different from the diameter of said storage holes peripherally arranged about said drum inside said wall, and at least one hole in each of said upper and lower plates positioned so that by rotating said drum about said shaft one of said storage holes or one of said guide holes may be selectively and separated brought into alignment with said upper and lower plate holes.

2. The apparatus claimed in claim 1 wherein said storage holes and guide holes have axes substantially parallel to said shaft.

3. A device for the continuous presentation of bone screws and like osteosynthesis fixation elements which comprises:

a drum housing having a central shaft;

a rotary drum having a side wall in said housing said rotary drum being rotatable about said shaft by contact with said side wall;

a plurality of cylindrical storage holes having the same diameter along substantially their entire length arranged around the periphery of said drum, said holes being shaped to store bone screws and like osteosynthesis fixation elements;

a plurality of cylindrical guide holes having a diameter different from the diameter of the storage holes on the periphery of the drum for receiving surgical tools, the center of said guide holes being the same distance from said shaft as the center of said storage holes;

said drum housing further comprising an upper plate having an access opening for the introduction of a surgical tool, the center of said access opening being located the same distance from the shaft axis as the storage holes;

a lower plate, having an outlet opening for an osteosynthesis fixation element, the center of the outlet opening being the same distance from the shaft axis as the center of said storage holes; and means for positioning said plates at a distance from one another permitting rotation of the drum between the plates;

said device further comprising a filling hole in the upper plate for supplying fixation elements to the storage holes, the center of the filling hole being arranged at the same distance from the shaft as the storage and guide holes, but offset circumferentially from said storage and guide holes.

4. Device according to claim 1, wherein the lower plate has a tissue-protection sleeve connected to the outlet opening and extending downwardly parallel to the shaft.

5. Device according to claim 1, wherein the upper plate has a drill bushing connected to said access opening and extending upwardly parallel to the shaft.

6. Device according to claim 1, and comprising indexing means for the stepwise positioning of the rotary drum.

7. The storage device claimed in claim 1, wherein said drum has indexing indentations corresponding to each hole of both series.

8. Apparatus for the storage and presentation of bone screws and like osteosynthesis elements comprising a housing having an upper plate and a lower plate, a shaft, a drum having a peripheral wall rotatably mounted on said shaft in said housing between said upper and lower plates, a plurality of substantially cylindrical storage holes peripherally arranged in said drum inside said peripheral wall, a plurality of substantially cylindrical guide holes having a diameter different from the diameter of said storage holes peripherally arranged about said drum inside said wall, the center of said guide holes being the same distance from said shaft as the center of said storage holes, and at least one hole in each of said upper and lower plates positioned so that by rotating said drum about said shaft, one of said storage holes or one of said guide holes may be brought into alignment with said plate holes.

9. Apparatus for the storage and presentation of bone screws and like osteosynthesis elements comprising a housing having an upper plate and a lower plate, a shaft, a drum having a peripheral wall rotatably mounted in said housing between said upper and lower plates, a plurality of substantially cylindrical storage holes peripherally arranged in said drum inside said peripheral wall, a plurality of substantially cylindrical guide holes having a diameter different from the diameter of said storage holes peripherally arranged about said drum inside said wall, at least one hole in each of said upper and lower plates positioned so that by rotating said drum about said shaft, one of said storage holes or one of said guide holes may be selectively and separate brought into alignment with said upper and lower plate holes and a handle extending from said housing.

* * * * *

UNITED STATES PATENT AND TRADEMARK OFFICE
CERTIFICATE OF CORRECTION

PATENT NO.   : 5,445,641

DATED        : August 29, 1995

INVENTOR(S)  : Robert Frigg and Rudolf Ambuhl

It is certified that error appears in the above-identified patent and that said Letters Patent is hereby corrected as shown below:

Title page,   item [73],   Assignee should read:   "Synthes (U.S.A.)".

Col. 4,   line 52,   (Claim 1) cancel "separated" and substitute --separately--.

Col. 6,   line 34,   (Claim 9) cancel "separate" and substitute --separately--.

Signed and Sealed this

Thirtieth Day of July, 1996

Attest:

BRUCE LEHMAN

*Attesting Officer*    *Commissioner of Patents and Trademarks*